United States Patent [19]

Vidal et al.

[11] Patent Number: 5,263,944
[45] Date of Patent: Nov. 23, 1993

[54] ADAPTER SEAL FOR LAPAROSCOPIC CANNULA

[75] Inventors: Claude A. Vidal, Santa Barbara; Russell J. Redmond; Alan K. Plyley, both of Goleta; John M. Barker, Ventura, all of Calif.; David L. Robbins, Roseville, Minn.

[73] Assignee: Minnesota Mining and Manufacturing Company, St. Paul, Minn.

[21] Appl. No.: 949,388

[22] Filed: Sep. 22, 1992

[51] Int. Cl.⁵ .............................................. A61M 5/00
[52] U.S. Cl. ...................................... 604/256; 604/167
[58] Field of Search ........................ 604/167, 256, 247

[56] References Cited

U.S. PATENT DOCUMENTS

| | | | |
|---|---|---|---|
| 3,860,006 | 1/1975 | Patel | 128/347 |
| 3,990,472 | 11/1976 | Etes | 604/247 |
| 3,994,287 | 11/1976 | Turp et al. | 128/6 |
| 4,177,814 | 12/1979 | Knepshield et al. | 128/348 |
| 4,240,411 | 12/1980 | Hosono | 128/4 |
| 4,424,833 | 1/1984 | Spector et al. | 137/849 |
| 4,473,067 | 9/1984 | Schiff | 128/1 |
| 4,601,710 | 7/1986 | Moll | 604/165 |
| 4,626,245 | 12/1986 | Weinstein | 604/167 |
| 4,654,030 | 3/1987 | Moll et al. | 604/165 |
| 4,655,752 | 4/1987 | Honkanen et al. | 604/256 |
| 4,715,360 | 12/1987 | Akui et al. | 604/256 |
| 4,895,565 | 1/1990 | Hillstead | 604/167 |
| 4,917,668 | 4/1990 | Haindl | 604/167 |
| 4,929,235 | 5/1990 | Merry et al. | 604/167 |
| 4,943,280 | 7/1990 | Lander | 604/169 |
| 4,960,412 | 10/1990 | Fink | 604/167 |
| 5,104,383 | 4/1992 | Shichman | 604/167 |
| 5,114,408 | 5/1992 | Fleischhaker et al. | 604/167 |
| 5,129,885 | 7/1992 | Green et al. | 604/164 |
| 5,141,498 | 8/1992 | Christian | 604/167 |
| 5,152,754 | 10/1992 | Plyley et al. | 604/164 |
| 5,197,955 | 3/1993 | Stephens et al. | 604/167 |

FOREIGN PATENT DOCUMENTS

| | | |
|---|---|---|
| 0113520 | 7/1984 | European Pat. Off. . |
| 0424002 | 4/1991 | European Pat. Off. . |
| 1482857 | 8/1977 | United Kingdom . |

OTHER PUBLICATIONS

Brochure entitled "The Source of Laparoscopic Innovation ORIGIN"; ORIGIN Medsystems, Inc.; OM-SLIT1 Rev. A 022592, 1992.
Brochure entitled "Richard Wolf-Yoon System for Ring Application"; Richard Wolf Medical Instruments Corp.; United States Surgical Corporation; 1988.

*Primary Examiner*—Paul J. Hirsch
*Attorney, Agent, or Firm*—Gary L. Griswold; Walter N. Kirn; Jeffrey J. Hohenshell

[57] ABSTRACT

An adapter seal adapted to facilitate the use of a small instrument within a laparoscopic cannula. The adapter seal comprises a body portion formed of elastomeric material, and a relatively rigid insertion guide mounted on the body portion The body portion has an aperture therein adapted to sealingly engage and support the small instrument while permitting movement of the instrument through the aperture The insertion guide has a wall forming a generally conical passageway for guiding small instruments toward the aperture of the body portion. A tether may be provided for holding the adapter seal adjacent the cannula when the body portion is disconnected from the cannula, and the insertion guide may be color-coded to indicate the size aperture through the body portion of the adapter seal.

20 Claims, 2 Drawing Sheets

ADAPTER SEAL FOR LAPAROSCOPIC CANNULA

This invention relates to a device useful in laparoscopic surgery, and more particularly to an improved adapter seal for a cannula used in laparoscopic surgery.

BACKGROUND OF THE INVENTION

A trend in modern medicine is to treat the body without invasive procedures, if possible, because invasive procedures inflict trauma on the patient, and because when the skin is broken the risk of infection to the patient, or others by the patient, increases substantially. When surgery must be performed, it is frequently desirable to use "minimally invasive" procedures as much as possible.

One type of "minimally invasive" procedure is laparoscopic surgery, in which a cannula facilitates using specially-designed surgical instruments to visualize and operate on the interior of the body through a small incision in the patient's body (e.g., through the abdominal wall). In this procedure, a trocar mounted in the cannula helps in introducing the cannula into the peritoneal cavity, which is inflated with carbon dioxide gas to increase the working area available inside the peritoneum. It is desirable to prevent the escape of this gas during the procedure in order to keep the peritoneal cavity inflated sufficiently to maintain room for manipulating surgical instruments. Accordingly, it is desirable to have an air tight seal between the cannula, and the trocar and other surgical instruments used in the cannula.

Separate adapter seals are available from trocar manufacturers that permit the surgeon to use smaller instruments in cannulae designed for larger instruments. Typically, such adapter seals are handed to the surgeon by a nurse, and then snapped into position on the cannula. When the surgeon is done using the small instrument and desires to use a larger instrument, the adapter seal is removed from the cannula and returned to the nurse. Since surgical site and through which surgical instruments are inserted into the cannula.

Generally, an adapter seal of the invention comprises a body portion formed of an elastomeric material, which is adapted for mounting on the proximal end of the cannula. The body portion of the adapter seal has an aperture therein adapted to sealingly engage and support the small instrument while permitting movement of the instrument through the aperture. An insertion guide is mounted on the body portion, and is adapted to guide the small instrument toward the aperture. The insertion guide is relatively rigid in comparison with the body portion. The insertion guide has a wall forming a generally conical passageway for guiding small instruments toward the aperture of the body portion.

Preferably, the adapter seal further includes a tether extending from the body portion of the adapter seal for securely attaching the adapter seal to the cannula. The tether permits the body portion of the adapter seal to be moved between a first position, securely attached to the cannula, yet away from the bore of the cannula, to a second position, wherein the body portion is mounted adjacent the proximal end of the cannula. In the second position, the aperture of the body portion of the adapter seal is substantially aligned with the bore of the cannula, and the proximal end of the bore of the cannula is sealed by the body portion except to flow through the aperture of the body portion. Most preferably, the end of the tether opposite the body portion has a loop thereon adapted to engage the cannula to securely attach the adapter seal to the cannula.

The tether facilitates removing the body portion of the adapter seal from the cannula in order to use a larger surgical instrument while keeping the adapter seal readily available to allow re-connection of the adapter seal to the cannula before a small surgical instrument is used. The tether also reduces the risk of rendering the adapter seal non-sterile when moving it away from the bore of the cannula.

Also, preferably, the adapter seal is adapted for use on a laparoscopic cannula of the type having an annular rim generally adjacent the proximal end of the bore of the cannula. The adapter seal may be so adapted by providing a generally annular rim on the body portion, with a channel formed in the annular rim of the body portion for sealingly engaging the annular rim of the cannula to mount the body portion in its second position on the cannula.

Most preferably, a tab is mounted on the annular rim of the body portion. The tab is adapted to be manually grasped to facilitate removing the body portion from its second position.

The insertion guide is preferably substantially harder than the body portion, and is positioned along the outside surface of the body portion to help protect the body portion from the surgical instruments, which may be very sharp (e.g., a trocar). For example, the loop, tether, body portion, annular rim and tab may be integrally molded of elastomeric material, and the insertion guide may be molded of substantially rigid thermoplastic or thermoset material. Most preferably, the insertion guide provides a lower coefficient of friction than the body portion to help guide the surgical instruments toward the aperture.

In another preferred aspect of the invention, the insertion guide is colored to provide an indication of the size of aperture provided in the body portion. A plurality of adapter seals having different size apertures may be provided for use with one cannula, with each different size aperture being indicated by a different color. Most preferably, the insertion guide is brightly colored for greater visual contrast so as to make it more recognizable even in very low light conditions.

Other features will be pointed out hereinafter.

BRIEF DESCRIPTION OF THE DRAWING

The invention Will be further described With reference to the drawing wherein corresponding reference characters indicate corresponding parts throughout the several views of the drawing, and wherein.

DETAILED DESCRIPTION OF A PREFERRED EMBODIMENT

Figure 1:
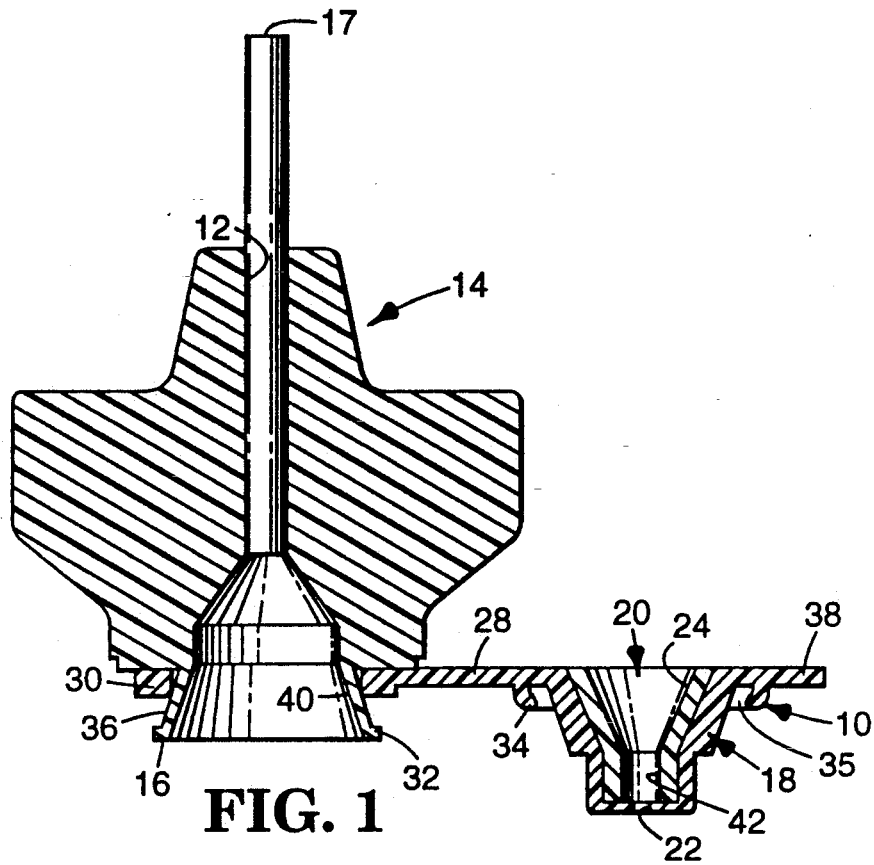
FIG. 1 is a cross-sectional view of an adapter seal of the invention attached to a laparoscopic cannula when the adapter seal is not in use.

Now referring to the drawing, an adapter seal of the invention is designated in its entirety by the reference numeral 10. The adapter seal 10 is adapted for facilitating the use of a small instrument (not shown) within the bore 12 of a cannula 14 of the type used in laparoscopic surgery. Laparoscopic surgery is surgery in which an internal body cavity (e.g., peritoneal cavity) is inflated with gas (typically carbon dioxide) to facilitate minimally invasive surgical manipulation of the organs or tissue in that body cavity. Typically, a separate cannula (not shown) is used for insufflation of the body cavity, but alternatively a suitable means, such as a stopcock (not shown), can be provided on the cannula 14 for insufflation of the body cavity. One type of separate cannula used for inflating a body cavity is described in co-assigned U.S. Pat. application Ser. No. 07/808,152, filed Dec. 13, 1991, entitled "Locking Penumoneedle," Thomas T. Banks and William A. Mittelstadt, which is incorporated herein by reference.

The cannula 14 has a proximal end 16 adapted to remain outside the surgical site, and a distal end 17 it is frequently necessary to alternate between small and large instruments during the same procedure, the repeated handling of the adapter seal can become an inconvenience to the surgical team.

In the subdued light used in laparoscopic operating theaters, it may be difficult to identify the proper size tool and to accurately position instruments for insertion through the cannula. Under these low light conditions, it may not be easy to locate the proper equipment (e.g., seal) or see identification marks on equipment. Current adapter seals provide a small target to the surgeon who is inserting the instrument into the trocar, which can lead to frustration during surgery.

U.S. Pat. No. 5,104,383 (Shichman) discloses a trocar adapter seal and method of use. That adapter seal is mounted on the proximal end of a laparoscopic cannula, and comprises an elastomeric seal and a substantially flat stabilizer plate formed of resilient plastic material such as ABS polymer. An adapter seal of that general type is available from United States Surgical Corp., Norwalk, Conn.

Origin Medsystems, Inc., San Carlos, Calif., sells a cannula having built in converters for converting the size of the proximal opening of the cannula.

SUMMARY OF THE INVENTION

This invention provides an adapter seal adapted for sealing between a laparoscopic cannula and a small surgical instrument (e.g., trocar) being used through the cannula. The adapter seal facilitates using more than one size surgical instrument while maintaining a reasonably gas tight seal in the cannula. The adapter seal also helps guide the small surgical instrument into the bore of the cannula so that less attention is required with respect to the initial step of introducing the small instrument into the cannula. The adapter seal is designed to seal the proximal end of the bore of the cannula, which is the end of the cannula that remains outside the adapted to be inserted into a body cavity to facilitate using surgical instruments within the body cavity. The central bore 12 extends between the proximal and distal ends 16 and 17 of the cannula 14.

Trocars and other small surgical instruments are inserted into the proximal end 16 of the cannula 14, through the bore 12, and into the body cavity (not shown). One trocar of the general type that may be used in the cannula 14 is described in U.S. Pat. application Ser. No. 07/657,105, filed Feb. 15, 1991, now U.S. Pat. No. 5,152,754 (Plyley et. al.), which is incorporated herein by reference. Trocars of that and other types generally have a plurality of sharp edges diverging from the sharp, pointed tip of the trocar.

Generally, the adapter seal 10 comprises a body portion 18 formed of an elastomeric material, and an insertion guide 20 mounted on the body portion 18. The body portion 18 is adapted for mounting on the proximal end 16 of the cannula 14. The body portion 18 has a circular aperture 22 therein adapted to sealingly engage and support the shaft of a small instrument (not shown) while permitting movement of the instrument through the aperture 22. The insertion guide 20, which is relatively rigid in comparison with the body portion 18, is adapted to guide the small instrument toward the aperture 22. The insertion guide 20 has a wall 24 forming a generally conical passageway (also 24) for guiding small instruments toward the aperture 22 of the body portion 18. The wall surface 24 is preferably generally lubricous (i.e., has a low coefficient of friction), for example, due to the surface properties of the material of the insertion guide 20 itself, or by application of a lubricant, such as silicone oil.

Preferably, a suitable means 26 is provided for attaching the adapter seal 10 to the cannula 14 such that the body portion 18 is movable from a first position (FIG. 1), securely attached to the cannula 14, yet away from the bore 12, to a second position (FIG. 2), wherein the body portion 18 is mounted adjacent the proximal end of the cannula 14. In the second position, the aperture 22 of the body portion 18 is substantially aligned with the bore 12 of the cannula 14, and the proximal end 16 of the bore 12 of the cannula 14 is sealed by the body portion 18 (except to flow through the aperture 22 of the body portion 18).

Conveniently, the means 26 for attaching the adapter seal 10 to the cannula 14 may comprise a tether 28 extending from the body portion 18, with the end of the tether 28 opposite the body portion 18 having a loop 30 thereon. The loop 30 is adapted to engage the cannula 14 to securely attach the adapter seal 10 to the cannula 14 (adjacent annular rim 32 of the cannula) while permitting the body portion 18 to be moved between its first and second positions. The inner diameter of the loop 30 is smaller than the outer diameter of the annular rim 32 of the cannula 14 to securely retain the loop 30 on the proximal end 16 of the cannula 14.

The tether 28 and loop 30 keep the adapter seal readily available to allow connection or re-connection of the body portion 18 of the adapter seal 10 to the cannula 14 before a small surgical instrument is used. The tether and loop 30 also reduce the risk of rendering the adapter seal 10 nonsterile when moving it away from the bore 12 of the cannula 14. The elastomeric material of the loop 30 allows the loop 30 to be stretched sufficiently to completely remove the adaptor seal 10 from the cannula 14 when that is desired.

The body portion 18 includes a generally annular rim 34 defining a channel 35 for sealingly engaging the annular rim 32 of the cannula 14 to mount the body portion 18 in its second position (FIG. 2) on the cannula 14. The annular rim 32 of the cannula 14 most preferably defines an annular channel 36 having a width approximately equal to the combined thicknesses of the loop 30 and annular rim 34 of the adapter seal 10. The arrangement is such that the loop 30 and the annular rim 34 of the adapter seal 10 are sized to allow both to be held on the cannula 14 by the rim 32 of the cannula 14.

A tab 38 is preferably mounted on the annular rim 34 of the body portion 1B. The tab 38 is adapted to be manually grasped to facilitate removing the body portion 18 from its second position (FIG. 1).

Most preferably, the loop 30, tether 28, body portion 18, annular rim 34 and tab 38 are integrally molded of elastomeric material. One elastomeric material that is believed to be suitable is medical grade silicone rubber having a durometer of approximately 55 on the Shore A scale.

Preferably, the insertion guide 20 has a lower coefficient of friction than the body portion 18 and is substantially harder than the body portion 18. For example, the insertion guide 20 may have a hardness of approximately 100-120 on the Rockwell R scale. The insertion guide 20 is designed to allow the sharp tips of laparoscopic instruments to slide toward the aperture 22 of the adapter seal 10 with less risk of snagging than would be the case if the tips engaged the elastomeric body portion 18.

The insertion guide 20 is molded of substantially rigid thermoplastic or thermoset material, such as nylon, acetal resin, polyphenylene oxide, and/or acrylonitrile-butadiene-styrene (ABS) resin. Suitable acetal resin is available under the trade designation "DELRIN" from E. I. DuPont de Nemours and Company, Wilmington, DE, and suitable polyphenylene oxide is available under the trade designation "NORYL" from General Electric Company, Pittsfield, Mass.

Figure 2:
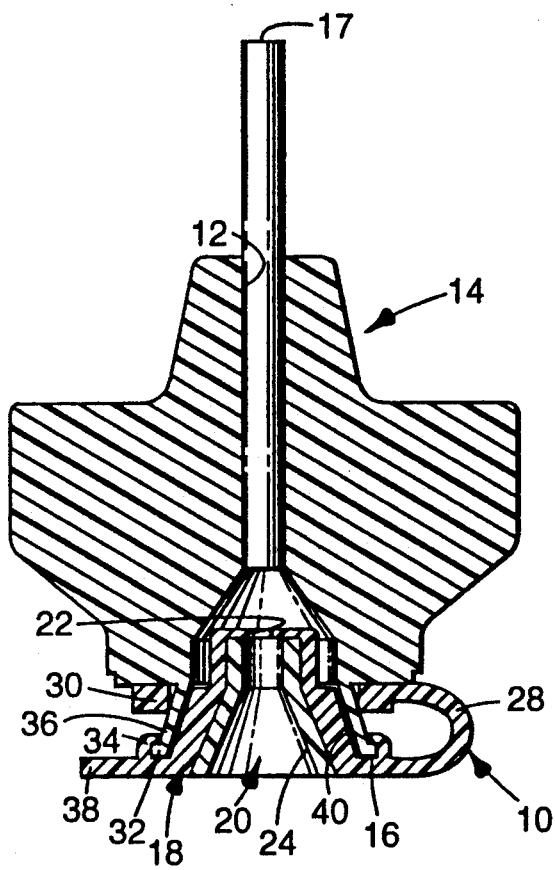
FIG. 2 is a cross-sectional view similar to FIG. 1 showing the adapter seal mounted on the cannula for use.
Figure 3:
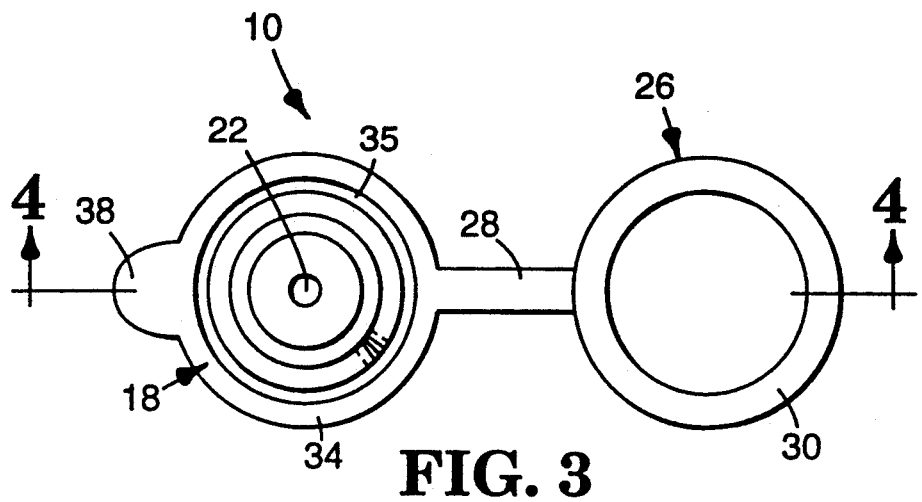
FIG. 3 is a bottom plan view of the adapter seal of FIGS. 1-2.
Figure 4:
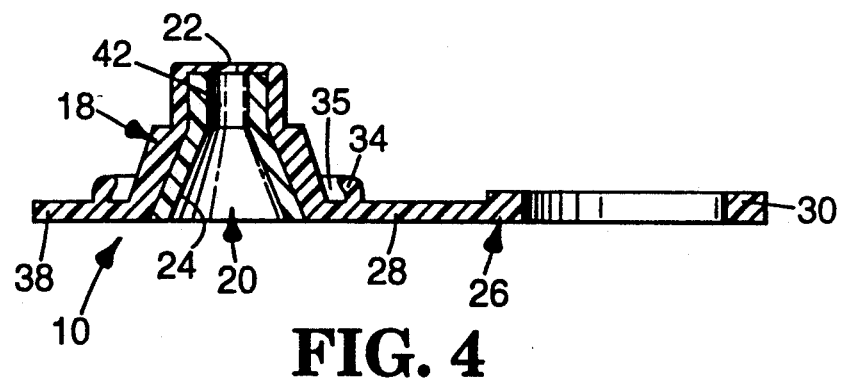
FIG. 4 is a cross-sectional view substantially along line 4—4 of FIG. 3.

The conical passageway 24 of the insertion guide 20 defines an axial direction of the adapter seal 10, and the aperture 22 of the body portion 18 is positioned in the axial inward direction relative to the rim 34 of the body portion 18. As illustrated in FIG. 2, the arrangement is preferably such that the elastomeric body portion 18 is sandwiched against surface of the conical portion 40 of the bore 12 of the cannula 14 by the conical insertion guide 20.

The insertion guide 20 may be provided with a relatively short cylindrical portion 42 extending axially inwardly from the conical passageway 24. For example, the cylindrical portion 42 may have a length in the axial direction approximately half of the length of the conical portion 24. As used herein, "conical" is intended to include frustoconical. The inner diameter of the cylindrical portion 42 is such that the corresponding size small instrument is closely received in the cylindrical portion 42.

The insertion guide 20 is mounted on the side of the body portion 18 that is adapted to face away from the cannula 14 in use of the adapter seal 10, and the conical-passageway-defining walls 24 of the insertion guide 20 converge inwardly in the direction toward the bore 12 of the cannula 14 in use of the adapter seal 10. The arrangement is such that the relatively hard material of the insertion guide 20 protects the softer material of the body portion 18 from frequently sharp edges on trocars and other surgical instruments while guiding such trocars and instruments into the aperture 22.

Preferably, the insertion guide 20 is colored to provide an indication of the size of aperture 22 provided in the body portion 18. For example, the adapter seals 10 may be provided in a plurality of standard sizes, with each size being indicated by a different color insertion guide 20 that is easily identifiable in low light conditions. Most preferably, the insertion guide 20 is brightly colored for greater visual contrast so as to make it more recognizable even in very low light conditions.

OPERATION

As is conventionally the case, a relatively large trocar (not shown) is introduced through the bore 12 of the cannula 14 before introducing the distal end 17 of the cannula 14 into the patient's body cavity (not shown). This trocar would substantially completely take up the bore 12 of the cannula 14, and is preferably sealed by a non-removable, permanent elastomeric seal (not shown) in a proximal portion of the bore 12 of the cannula. The cannula 14 may also be provided with a second seal (not shown) of conventional design (e.g., a flap seal) that seals the bore 12 completely when the trocar is removed after the distal end 17 of the cannula 14 has been introduced into the body cavity.

After the cannula 14 is in position into the body cavity, it may be desirable to use a smaller surgical instrument, such as another trocar, clip applier, stapler, cutting instrument, etc., but it is still important to maintain an airtight seal to prevent the escape of carbon dioxide gas through the cannula 14. This may be accomplished by placing the body portion 18 of the adapter seal 10 on the proximal end 16 of the cannula 14, with the rim 34 of the body portion 18 sealingly engaging the rim 32 of the cannula. The desired adapter seal 10 can be held conveniently adjacent the cannula 14 with the tether 28 so that the surgeon can place the body portion 18 on the cannula 14 without searching or asking a nurse for the adaptor seal 10.

It is also contemplated that the annular rim 32 of the cannula 14 could be adapted to hold more than one color-coded adapter seal 10 in convenient proximity to the cannula 14. For example, the annular channel 36 of the cannula 14 may be sufficiently wide to receive two or three loops 30.

As various changes could be made in the above constructions without departing from the scope of the invention, it is intended that all matter contained in the description above or shown in the accompanying drawing be interpreted as illustrative and not in a limiting sense.

We claim:

1. An adapter seal adapted for facilitating the use of a small instrument within the bore of a cannula of the type used in laparoscopic surgery, the cannula having a proximal end adapted to remain outside the surgical site through which instruments may be inserted, the adapter seal comprising:

a body portion formed on an elastomeric material and being adapted for removably mounting on the proximal end of the cannula, the body portion having an aperture therein adapted to sealingly engage and support the small instrument while permitting movement of the instrument through the aperture; and an insertion guide mounted on the body portion adapted to guide the small instrument toward the aperture, the insertion guide being relatively rigid in comparison with the body portion, the insertion guide having a wall forming a generally conical passageway for guiding small instruments toward the aperture of the body portion.

2. An adapter seal adapted for facilitating the use of a small instrument within the bore of a cannula of the type used in laparoscopic surgery, the cannula of the type used in laparoscopic surgery, the cannula having a proximal end adapted to remain outside the surgical site through which instruments may be inserted, the adapter seal comprising:

a body portion formed of an elastomeric material and being adapted for mounting on the proximal end of the cannula, the body portion having an aperture therein adapted to sealingly engage and support the small instrument while permitting movement of the instrument through the aperture;

an insertion guide mounted on the body portion adapted to guide the small instrument toward the aperture, the insertion guide being relatively rigid in comparison with the body portion, the insertion guide having a wall forming a generally conical passageway for guiding small instruments toward the aperture of the body portion; and means for attaching the adapter seal to the cannula such that the body member is movable from a first position, securely attached to the cannula, yet away from the bore, to a second position, wherein the body portion is mounted adjacent the proximal end of the cannula such that the aperture of the body portion is substantially aligned with the bore of the cannula, and the proximal end of the bore of the cannula is sealed by the body portion except to flow through the aperture of the body portion.

3. An adapter seal according to claim 2 adapted to be used with a laparoscopic cannula of the type having an annular rim generally adjacent the proximal end of the bore of the cannula; the means for attaching comprising:

a tether extending from the body portion, the end of the tether opposite the body portion having a loop thereon adapted to engage the cannula to securely attach the adapter seal to the cannula while permitting the body portion to be moved between its first and second positions; and a generally annular rim on the body portion having a channel for sealingly engaging the annular rim of the cannula to mount the body portion in its second position on the cannula;

the adapter seal further comprising a tab mounted on the annular rim of the body portion, the tab being adapted to be manually grasped to facilitate removing the body portion from its second position.

4. An adapter seal according to claim 3 wherein the insertion guide is substantially harder than the body portion, the loop, tether, body portion, annular rim and tab being integrally molded of elastomeric material, and the insertion guide being molded of substantially rigid thermoplastic or thermoset material.

5. An adapter seal according to claim 4 wherein the loop and the annular rim of the adapter seal are sized to allow both be held on the cannula by the rim of the cannula.

6. An adapter seal according to claim 5 wherein the elastomeric material comprises silicone rubber, the insertion guide comprising material selected from the group comprising nylon, acetal resin, and polyphenylene oxide.

7. An adapter seal according to claim 3 wherein the conical passageway of the insertion guide defines an axial direction of the adapter seal, the aperture of the body portion being positioned in the axial inward direction relative to the rim of the body portion.

8. An adapter seal according to claim 1 wherein the insertion guide has a lower coefficient of friction than the body portion, the insertion guide being mounted on the side of the body portion that is adapted to face away from the cannula in use of the adapter seal.

9. An adapter seal according to claim 8 wherein conical-passageway-defining walls of the insertion guide converge inwardly in the direction toward the bore of the cannula in use of the adapter seal.

10. An adapter seal according to claim 1 wherein the insertion guide is colored to provide an indication of the size of aperture provided in the body portion.

11. A combination of a cannula used in laparoscopic surgery and an adapter seal for facilitating the use of a small instrument within the cannula, the combination comprising:

a cannula having proximal and distal ends, and a central bore extending between the proximal and distal ends of the cannula, the distal end of the cannula being adapted to be inserted into a body cavity to facilitate using surgical instruments within the body cavity, the proximal end of the cannula being adapted to remain outside the body cavity and through which surgical instruments may be inserted; and an adapter seal comprising a body portion formed of an elastomeric material and being adapted for removably mounting on the proximal end of the cannula, the body portion having an aperture therein adapted to sealingly engage and support a small surgical instrument while permitting movement of the instrument through the aperture, and an insertion guide mounted on the body portion adapted to guide the small surgical instrument toward the aperture, the insertion guide being relatively rigid in comparison with the body portion, the insertion guide having a wall forming a generally conical passageway for guiding small surgical instruments toward the aperture of the body portion.

12. The combination according to claim 11 wherein the adapter seal further comprises means for attaching the adapter seal to the cannula such that the body member is movable from a first position, securely attached to the cannula, yet away from the bore of the cannula, to a second position, wherein the body portion is mounted adjacent the proximal end of the cannula such that the aperture of the body portion is substantially aligned with the bore of the cannula and the proximal end of the bore of the cannula is sealed by the body portion except to flow through the aperture of the body portion.

13. The combination according to claim 12 wherein the cannula further includes an annular rim generally adjacent the proximal end of the bore of the cannula; and the means for attaching the adapter seal to the cannula comprising:

a tether extending from the body portion, the end of the tether opposite the body portion having a loop thereon adapted to engage the cannula to securely attach the adapter seal to the cannula while permitting the body portion to be moved between its first and second positions; and a generally annular rim on the body portion having a channel for sealingly engaging the annular rim of the cannula to mount the body portion in its second position on the cannula;

the adapter seal further comprising a tab mounted on the annular rim of the body portion, the tab being adapted to be manually grasped to facilitate removing the body portion from its second position.

14. The combination according to claim 13 wherein the insertion guide is substantially harder than the body portion, the loop, tether, body portion, annular rim and tab being integrally molded of elastomeric material, and the insertion guide being molded of substantially rigid thermoplastic or thermoset material.

15. The combination according to claim 14 wherein the elastomeric material comprises silicone rubber, the insertion guide comprising material selected from the group comprising nylon, acetal resin, and polyphenylene oxide.

16. The combination according to claim 15 wherein the loop and the annular rim of the adapter seal are sized to allow both be held on the cannula by the rim of the cannula.

17. The combination according to claim 13 wherein the conical passageway of the insertion guide defines an axial direction of the adapter seal, the aperture of the body portion being positioned in the axial inward direction relative to the rim of the body portion.

18. The combination according to claim 11 wherein the insertion guide has a lower coefficient of friction than the body portion, the conical-passageway-defining walls of the insertion guide converging inwardly in the direction toward the bore of the cannula in use of the adapter seal.

19. The combination according to claim I1 wherein the insertion guide is colored to provide an indication of the size of aperture provided in the body portion.

20. The combination according to claim 19 further comprising a plurality of the adapter seals, each having a different size aperture in its body portion and an insertion guide colored to provide an indication of the size aperture that is provided in the body portion.

* * * * *